US00PP37332P2

(12) United States Plant Patent
de Vos

(10) Patent No.: US PP37,332 P2
(45) Date of Patent: Mar. 17, 2026

(54) ***HYDRANGEA* PLANT NAMED 'HORE9311'**

(50) Latin Name: *Hydrangea macrophylla*
Varietal Denomination: HORE9311

(71) Applicant: KWEKERIJ LENDERT de VOS B.V., Reeuwijk (NL)

(72) Inventor: Lendert de Vos, Reeuwijk (NL)

(73) Assignee: KWEKERIJ LENDERT de VOS B.V., Reeuwijk (NL)

( * ) Notice: Subject to any disclaimer, the term of this patent is extended or adjusted under 35 U.S.C. 154(b) by 0 days.

(21) Appl. No.: 19/030,145

(22) Filed: Jan. 17, 2025

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 5/00; A01H 6/48
See application file for complete search history.

(56) References Cited

PUBLICATIONS

Facebook Green House Post 2024 retrieved on Apr. 1, 2025 at https://www.facebook.com/story.php/?story_fbid=897845425698239&id=100064183688066&_rdr, one page. (Year: 2024).*
Floral Daily, NL: Astilibe simplicifolia 'Pretty in Pink' winner of the Green Retail Award for Best Novelty—Jun. 2024, retrieved on Mar. 31, 2025 at https://www.floraldaily.com/article/9634514/nl-astilbe-simplicifolia-pretty-in-pink-winner-of-the-green-retail-award-for-best-novelty-june-2024/, 3 pp. (Year: 2024).*
Google translate of Facebook retrieved on Apr. 1, 2025 at https://www.google.com/search?q=translate&rlz=1C1GCEA_enUS1032US1033&oq=translate&gs_lcrp=EgZjaHJvbWUyDwgAEEUYORiDARixAxiA . . . 3 pp. (Year: 2025).*

* cited by examiner

*Primary Examiner* — June Hwu
(74) *Attorney, Agent, or Firm* — C. Anne Whealy

(57) ABSTRACT

A new and distinct cultivar of *Hydrangea* plant named 'HORE9311', characterized by its relatively compact, upright to broadly spreading plant habit; relatively moderately vigorous growth habit; freely branching habit; strong and sturdy stems; freely flowering habit; panicles with double-type sterile flowers that are greenish white to white in color; and good postproduction longevity.

2 Drawing Sheets

Figure 1:
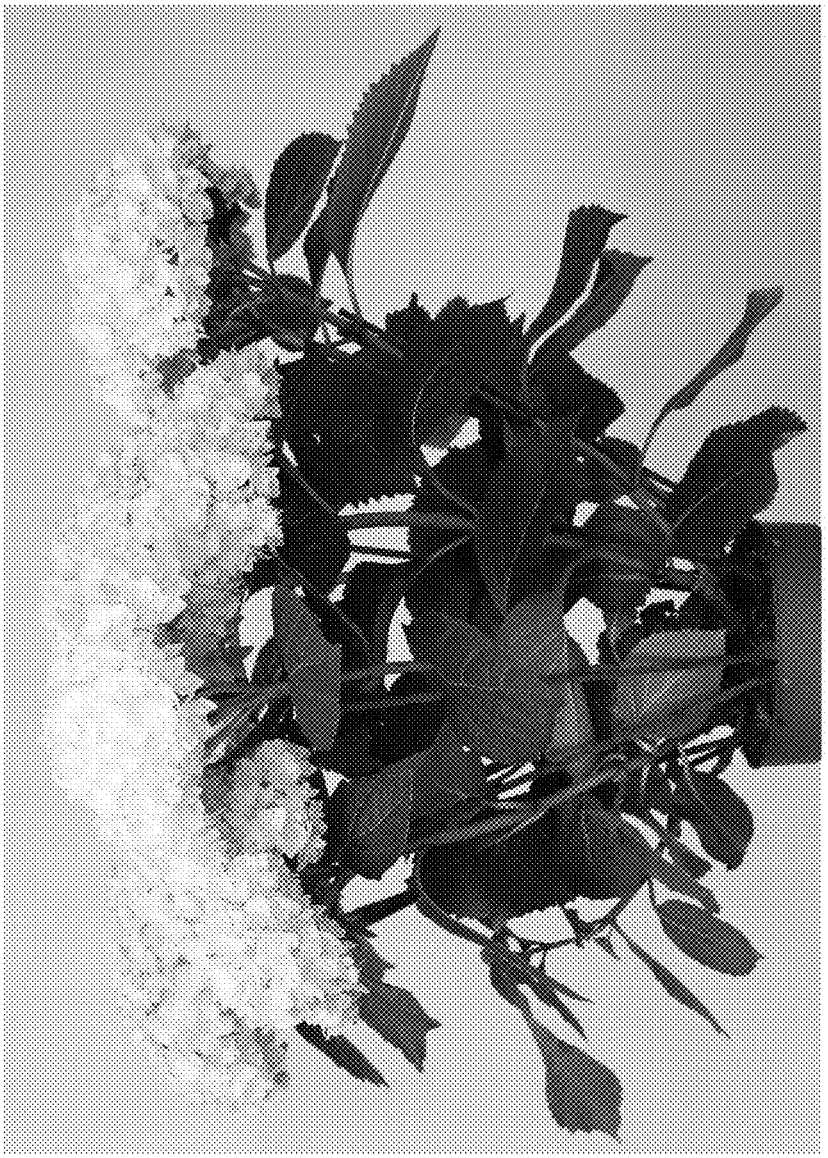

Botanical designation: *Hydrangea macrophylla.*
Cultivar denomination: 'HORE9311'.

CROSS-REFERENCED TO CLOSELY-RELATED APPLICATIONS

Title: *Hydrangea* Plant Named 'HORE9306'
Inventor: Lendert de Vos
Filed: Jan. 16, 2024

A United Kingdom Plant Breeder's Rights application for this plant was filed by the Applicant/Assignee of the instant application, Kwekerij Lendert de Vos of Reeuwijk, The Netherlands on Aug. 20, 2024, application number 23/882, and published on Sep. 1, 2024. Foreign priority is not claimed to this United Kingdom Plant Breeder's Rights application.

A European Community Plant Breeder's Rights application for this plant was filed by the Applicant/Assignee of the instant application, Kwekerij Lendert de Vos of Reeuwijk, The Netherlands on Sep. 24, 2024, application number 2024/2229, and published on Dec. 15, 2024. Foreign priority is not claimed to this European Plant Breeder's Rights application.

BACKGROUND OF THE INVENTION

The present invention relates to a new and distinct cultivar of *Hydrangea* plant, botanically known as *Hydrangea macrophylla*, commercially referred to as a Bigleaf *Hydrangea* and hereinafter referred to by the name 'HORE9311'.

The new *Hydrangea* plant is a product of a planned breeding program conducted by the Inventor in Reeuwijk, The Netherlands. The objective of the breeding program is to create new compact and strong *Hydrangea* plants with attractive inflorescences and good postproduction longevity.

The new *Hydrangea* plant originated from a cross-pollination in August, 2017 of a proprietary selection of *Hydrangea macrophylla* identified as code number 16-20161-02, not patented, as the female, or seed, parent with a proprietary of *Hydrangea macrophylla* identified as code number 16-20143-03, not patented, as the male, or pollen, parent. The new *Hydrangea* plant was discovered and selected as a single flowering plant from within the progeny of the stated cross-pollination in a controlled greenhouse environment in Reeuwijk, The Netherlands in August, 2019.

Asexual reproduction of the new *Hydrangea* plant by terminal vegetative cuttings since August, 2019 in a controlled greenhouse environment in Reeuwijk, The Netherlands has shown that the unique features of this new *Hydrangea* plant are stable and reproduced true to type in successive generations of asexual reproduction.

SUMMARY OF THE NEW PLANT

Plants of the new *Hydrangea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HORE9311'. These characteristics in combination distinguish 'HORE9311' as a new and distinct *Hydrangea* plant:

1. Relatively compact, upright to broadly spreading plant habit.
2. Relatively moderately vigorous growth habit.
3. Freely branching habit.
4. Strong and sturdy stems.
5. Freely flowering habit.
6. Panicles with double-type sterile flowers that are greenish white to white in color.
7. Good postproduction longevity.

Plants of the new *Hydrangea* can be compared to plants of the female parent selection. Plants of the new *Hydrangea* differ primarily from plants of the female parent selection in the following characteristics:

1. Plants of the new *Hydrangea* are more compact than plants of the female parent selection.
2. Plants of the new *Hydrangea* have double-type sterile flowers whereas plants of the female parent selection have single-type sterile flowers.
3. Flowers of plants of the new *Hydrangea* are sterile whereas flowers of plants of the female parent selection are fertile.

Plants of the new *Hydrangea* can be compared to plants of the male parent selection. Plants of the new *Hydrangea* differ primarily from plants of the male parent selection in the following characteristics:

1. Plants of the new *Hydrangea* are more compact than plants of the male parent selection.
2. Plants of the new *Hydrangea* have double-type sterile flowers whereas plants of the male parent selection have single-type sterile flowers.
3. Flowers of plants of the new *Hydrangea* are sterile whereas flowers of plants of the male parent selection are fertile.

Plants of the new *Hydrangea* can be compared to plants of *Hydrangea macrophylla* 'HORE9306', disclosed in U.S. Plant patent application Ser. No. 19/030,116. In side-by-side comparisons, plants of the new *Hydrangea* differ primarily from plants of 'HORE9306' in sterile flower color as plants of the new *Hydrangea* have whitish green to white-colored sterile flowers whereas plants of 'HORE9306' have pale purple-colored sterile flowers.

Plants of the new *Hydrangea* can be compared to plants of *Hydrangea macrophylla* 'Dancing Snow', disclosed in U.S. Plant Pat. No. 21,052. In side-by-side comparisons, plants of the new *Hydrangea* differ primarily from plants of 'Dancing Snow' in the following characteristics:

1. Plants of the new *Hydrangea* are more compact than plants of 'Dancing Snow'.
2. Plants of the new *Hydrangea* have smaller inflorescences than plants of 'Dancing Snow'.
3. Inflorescences of plants of the new *Hydrangea* are mophead types whereas inflorescences of plants of 'Dancing Snow' are lacecap types.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HORE9311' grown in a container.

Figure 2:
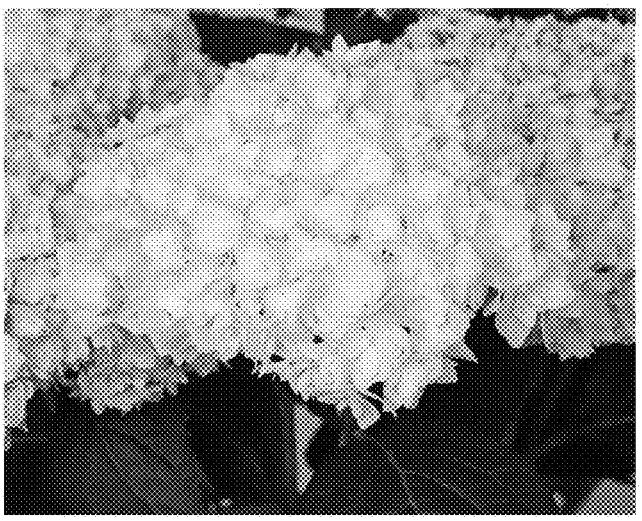

The photograph at the top of the second sheet (FIG. 2) is a close-up view of typical inflorescences of 'HORE9311'.

Figure 3:
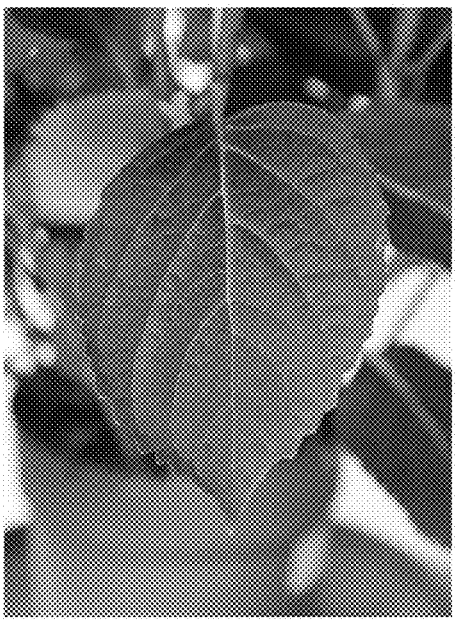

The photograph at the bottom of the second sheet (FIG. 3) is a close-up view of typical leaves of 'HORE9311'.

DETAILED BOTANICAL DESCRIPTION

Plants used in the aforementioned photographs and in the following description were grown during the summer in 14-cm containers in a glass-covered greenhouse in Reeuwijk, The Netherlands and under cultural practices typical of commercial *Hydrangea* production. During the production of the plants, day temperatures ranged from 20° C. to 35° C. and night temperatures ranged from 10° C. to 22°° C. Plants of the new *Hydrangea* were pinched one time and were 18 months old when the photographs and description were taken. In the following description, color references are made to The Royal Horticultural Society Colour Chart, Sixth Edition, except where general terms of ordinary dictionary significance are used. The new *Hydrangea* plant is not typically treated with aluminum sulfate to "blue" the flower color.

Botanical description: *Hydrangea macrophylla* 'HORE9311'.

Parentage:

*Female, or seed, patent*.—Proprietary selection of *Hydrangea macrophylla* identified as code number 16-20161-02, not patented.

*Male, or pollen, patent*.—Proprietary selection of *Hydrangea macrophylla* identified as code number 16-20143-03, not patented.

Propagation:

*Type cutting*.—By vegetative terminal cuttings.

*Time to initiate roots, summer*.—About 16 days at temperatures ranging from 20° C. to 30° C.

*Time to produce a rooted young plant, summer*.—About four months at temperatures ranging from 20° C. to 30° C.

*Root description*.—Medium in thickness; fibrous; typically light brown in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Relatively compact; upright to broadly outwardly spreading and mounding plant habit; overall shape, flattened globular; strong and sturdy stems; relatively moderately vigorous growth habit and moderate growth rate; about six months from propagation are required to produce small finished plants.

*Plant height*.—About 39 cm.

*Plant diameter or area of spread*.—About 56.8 cm.

Lateral branch description:

*Branching habit*.—Freely branching habit with about 13 lateral branches developing per plant; pinching is not required, but will enhance lateral branch development.

*Length*.—About 28.9 cm.

*Diameter*.—About 7 mm.

*Internode length*.—About 7.4 cm.

*Strength*.—Strong, sturdy.

*Aspect*.—Erect to about 60° from vertical.

*Texture*.—Smooth, glabrous; becoming woody with subsequent development.

*Color, developing*.—Close to 144A.

*Color, fully developed*.—Close to 144A; at the nodes, slightly tinged with close to 183B to 183C; when woody, close to 199B, N199A and N199B.

*Lenticels*.—Density: Sparse. Length: About 2 mm. Diameter: About 0.5 mm. Color: Close to N186C.

Leaf description:

*Arrangement*.—Opposite, simple.

*Length*.—About 13 cm.

*Width*.—About 9 cm.

*Shape*.—Broadly ovate to broadly elliptic.

*Apex*.—Apiculate.

*Base*.—Acute to rounded.

*Margin*.—Coarsely dentate-serrate.

*Texture and luster, upper surface*.—Smooth, glabrous; somewhat glossy.

*Texture and luster, lower surface*.—Smooth, glabrous; slightly rugose; slightly glossy.

*Venation pattern*.—Pinnate.

*Color*.—Developing leaves, upper surface: Close to NN137A. Developing leaves, lower surface: Close to 147B. Fully developed leaves, upper surface: Close to a blend of 147A and N189A; venation, close to 146D. Fully developed leaves, lower surface: Close to 147B; venation, close to 146D.

*Petioles*.—Length: About 2.9 cm. Diameter: About 3 mm. Texture and luster, upper and lower surfaces: Smooth, glabrous; slightly glossy. Color, upper surface: Close to 146D; marginal edges, close to 144A. Color, lower surface: Close to 146C.

Flower description:

*Flower type and habit*.—Rotate double-type sterile flowers arranged on dense terminal hemispherical panicles; panicles flattened globular in overall shape; sterile flowers face upright to outwardly to slightly downward; to date, fertile flower development has not been observed on plants of the new *Hydrangea*.

*Fragrance*.—None detected.

*Natural flowering season*.—Plants flower continuously for about three months; in garden in The Netherlands, plants flower from late spring into the late summer.

*Flower longevity*.—Good postproduction longevity; sterile flowers maintain good substance for about six weeks on the plant, sterile flowers persistent.

*Quantity of flowers*.—Freely flowering habit; about 550 sterile flowers per panicle.

*Panicle height*.—About 9.3 cm.

*Panicle diameter*.—About 16.9 cm.

*Panicle peduncles*.—Length: About 4.7 cm. Diameter: About 3.5 mm to 5 mm. Strength: Strong. Aspect: Primary peduncles, mostly erect; lateral peduncles, about 50° from primary peduncle axis. Texture and luster: Sparsely to moderately pubescent; matte. Color: Close to 144A; at the nodes, slightly tinged with close to 178A and 178B. Lenticels: Density: Sparse. Length: About 1 mm. Diameter: About 0.5 mm. Color: Close to 200C.

*Sterile flower buds*.—Length: About 7 mm. Diameter: About 1.2 cm. Shape: Cup-shaped. Color: Close to NN155D.

*Sterile flower diameter*.—About 2.2 cm.

*Sterile flower depth* (*height*).—About 9 mm.

*Petals, sterile flowers*.—To date, petal development has not been observed on sterile flowers of plants of the new *Hydrangea*.

*Sepals, sterile flowers*.—Quantity and arrangement: About 15 in multiple whorls. Length: About 1.3 mm. Width: About 1 cm. Shape: Broadly ovate to elliptic; mostly flat to slightly concave. Apex: Obtuse to broadly and bluntly acute. Base: Broadly attenuate. Margin: Entire. Texture and luster, upper and lower surfaces: Smooth, glabrous; matte. Color: When opening, upper surface: Close to NN155D. When opening, lower surface: Close to NN155C. Fully opened, upper surface: Close to 155C; with subsequent development, color becoming closer to 145A and 145B with narrow marginal edges, close to 157B. Fully opened, lower surface: Close to 155C; towards the apex, close to NN155A; with subsequent development, color becoming closer to 145B with narrow marginal edges, close to 157B.

*Pedicels, sterile flowers*.—Length: About 1.3 cm. Diameter: About 1 mm. Strength: Moderately strong. Aspect: About 40° from main peduncle axis Texture and luster: Moderately to densely pubescent; matte. Color: Close to NN155D.

*Reproductive organs, sterile flowers*.—Stamens: To date, stamen development has not been observed on plants of the new *Hydrangea*. Pistils: Pistil quantity per flower: Typically three. Pistil length: About 0.75 mm. Stigma shape: Club-shaped. Stigma color: Close to 155C. Style length: About 0.5 mm. Style color: Close to 145C. Ovary color: Close to 145C.

*Fruits and seeds*.—To date, fruit and seed development has not been observed on plants of the new *Hydrangea*.

Pathogen & pest resistance: Plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HORE9311' as herein illustrated and described.

* * * * *